United States Patent
Wagner et al.

(10) Patent No.: US 7,666,825 B2
(45) Date of Patent: *Feb. 23, 2010

(54) STABLE, PATTERNED MULTI-PHASED PERSONAL CARE COMPOSITION

(75) Inventors: Julie Ann Wagner, Cincinnati, OH (US); Karl Shiqing Wei, Mason, OH (US); Edward Dewey Smith, III, Mason, OH (US); Sanjeev Midha, Mason, OH (US); James Merle Heinrich, Fairfield, OH (US); Scott William Syfert, Ft. Mitchell, KY (US); Robert John Strife, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/197,866

(22) Filed: Aug. 5, 2005

(65) Prior Publication Data

US 2006/0079417 A1 Apr. 13, 2006

Related U.S. Application Data

(60) Provisional application No. 60/617,392, filed on Oct. 8, 2004, provisional application No. 60/628,015, filed on Nov. 15, 2004, provisional application No. 60/680,113, filed on May 12, 2005.

(51) Int. Cl.
*A61K 7/50* (2006.01)
(52) U.S. Cl. .................. 510/156; 510/421; 510/424; 510/426; 510/427; 510/499
(58) Field of Classification Search .................. None
See application file for complete search history.

(56) References Cited

U.S. PATENT DOCUMENTS

| | | |
|---|---|---|
| 3,479,429 A | 11/1969 | Morshauser et al. |
| 3,533,955 A | 10/1970 | Pader et al. |
| 3,937,811 A | 2/1976 | Papantoniou et al. |
| 4,159,028 A | 6/1979 | Barker et al. |
| 4,263,363 A | 4/1981 | Buck et al. |
| 4,335,103 A | 6/1982 | Baker et al. |
| 4,425,322 A | 1/1984 | Harvey et al. |
| 4,518,578 A | 5/1985 | Hayes et al. |
| 4,980,155 A | 12/1990 | Shah et al. |
| 5,059,414 A | 10/1991 | Dallal et al. |
| 5,228,912 A | 7/1993 | Driller et al. |
| 5,393,450 A | 2/1995 | Shana'a et al. |
| 5,455,035 A | 10/1995 | Guerrero et al. |
| 5,487,168 A | 1/1996 | Geiner et al. |
| 5,556,628 A | 9/1996 | Derian et al. |
| 5,584,409 A | 12/1996 | Narayanier |
| 5,612,307 A | 3/1997 | Chambers et al. |
| 5,635,171 A | 6/1997 | Nadaud et al. |
| 5,661,189 A | 8/1997 | Grievson et al. |
| 5,726,137 A | 3/1998 | Patel et al. |
| 5,851,978 A | 12/1998 | Shana'a |
| 5,914,117 A * | 6/1999 | Lavaud ....................... 424/401 |
| 5,929,019 A | 7/1999 | Puvvada et al. |
| 5,947,335 A | 9/1999 | Milio et al. |
| 5,952,286 A * | 9/1999 | Puvvada et al. ............. 510/417 |
| 5,965,500 A | 10/1999 | Puvvada |
| 6,150,312 A | 11/2000 | Puvvada et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,213,166 B1 | 4/2001 | Thibiant et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |
| 6,340,723 B1 | 1/2002 | Nita et al. |
| 6,383,999 B1 | 5/2002 | Coyle et al. |
| 6,426,326 B1 * | 7/2002 | Mitra et al. .................. 510/130 |
| 6,429,177 B1 | 8/2002 | Salmon et al. |
| 6,506,391 B1 | 1/2003 | Biatry |
| 6,517,939 B1 | 2/2003 | Ramin et al. |
| 6,534,456 B2 * | 3/2003 | Hayward et al. ............. 510/130 |

(Continued)

FOREIGN PATENT DOCUMENTS

CA 2246316 6/1998

(Continued)

OTHER PUBLICATIONS

XP 002332778 "Dove All Day Moisturizing Body Wash" Online URL: http://www.ewg.org/reports/skindeep2/report.php?type=Product&id=8801874.

(Continued)

*Primary Examiner*—Necholus Ogden, Jr.
(74) *Attorney, Agent, or Firm*—Mark A. Charles

(57) ABSTRACT

A multi-phase personal care composition is described that comprises a first visually distinct structured phase and a second visually distinct structured phase. The first visually distinct structured phase comprises a cleansing phase that includes about 2% to about 23.5%, by weight of the cleansing phase, of surfactant component. Preferably, the surfactant component comprises at least one branched anionic surfactant.

15 Claims, No Drawings

U.S. PATENT DOCUMENTS

| | | | |
|---|---|---|---|
| 6,534,457 B2 * | 3/2003 | Mitra | 510/130 |
| 6,673,755 B2 | 1/2004 | Wei et al. | |
| 2001/0036467 A1 | 11/2001 | Thibiant et al. | |
| 2002/0004468 A1 | 1/2002 | Hodge et al. | |
| 2002/0010110 A1 | 1/2002 | Hayward et al. | |
| 2003/0152540 A1 | 8/2003 | Putman et al. | |
| 2003/0161852 A1 | 8/2003 | Miller et al. | |
| 2003/0180246 A1 * | 9/2003 | Frantz et al. | 424/70.21 |
| 2003/0222100 A1 | 12/2003 | Husband et al. | |
| 2004/0048757 A1 | 3/2004 | Zhang et al. | |
| 2004/0048758 A1 | 3/2004 | Zhang et al. | |
| 2004/0057920 A1 | 4/2004 | Focht et al. | |
| 2004/0092415 A1 * | 5/2004 | Focht et al. | 510/130 |
| 2004/0105827 A1 | 6/2004 | Grimm et al. | |
| 2004/0158940 A1 | 8/2004 | Wells et al. | |
| 2004/0219119 A1 | 11/2004 | Wei et al. | |
| 2004/0223929 A1 | 11/2004 | Clapp et al. | |
| 2004/0223939 A1 | 11/2004 | Clapp et al. | |
| 2004/0223991 A1 | 11/2004 | Wei et al. | |
| 2004/0235693 A1 * | 11/2004 | Wei et al. | 510/130 |
| 2004/0235702 A1 | 11/2004 | Huntsman | |
| 2004/0242706 A1 | 12/2004 | Wiersema et al. | |
| 2004/0248748 A1 | 12/2004 | Wei et al. | |
| 2005/0020468 A1 * | 1/2005 | Frantz et al. | 510/424 |
| 2005/0100570 A1 | 5/2005 | Wei et al. | |
| 2005/0143269 A1 | 6/2005 | Wei et al. | |
| 2005/0192187 A1 | 9/2005 | Wagner et al. | |
| 2005/0192188 A1 | 9/2005 | Wagner et al. | |
| 2005/0192189 A1 | 9/2005 | Wagner et al. | |
| 2005/0238680 A1 | 10/2005 | Stella et al. | |
| 2005/0276768 A1 | 12/2005 | Wei et al. | |
| 2006/0002880 A1 | 1/2006 | Peffly et al. | |

FOREIGN PATENT DOCUMENTS

| | | | |
|---|---|---|---|
| DE | 196 50 952 A | 6/1998 | |
| DE | 198 54 086 A | 5/2000 | |
| EP | 0 078138 A2 | 5/1983 | |
| EP | 0 331617 B | 4/1992 | |
| EP | 1 108421 A2 | 6/2001 | |
| EP | 1 005849 B1 | 9/2001 | |
| EP | 1 064918 B1 | 9/2002 | |
| EP | 0 907345 B1 | 5/2003 | |
| GB | 1277324 A | 6/1972 | |
| JP | 2000229817 A | 8/2000 | |
| JP | 2002-128639 A | 5/2002 | |
| JP | 2002-138010 A | 5/2002 | |
| WO | WO 90/13283 A1 | 11/1990 | |
| WO | WO 94/10973 A1 | 5/1994 | |
| WO | WO 97/17938 A1 | 5/1997 | |
| WO | WO 98/27193 A1 | 6/1998 | |
| WO | WO 99/38489 A1 | 8/1999 | |
| WO | WO 99/38491 A1 | 8/1999 | |
| WO | WO 00/75240 A1 | 12/2000 | |
| WO | WO 01/01931 A1 | 1/2001 | |
| WO | WO 01/70193 A2 | 9/2001 | |
| WO | WO 01/70926 A1 | 9/2001 | |
| WO | WO 02/100358 A1 | 12/2002 | |
| WO | WO 03/055456 A1 | 7/2003 | |
| WO | WO 03/105796 A1 | 12/2003 | |
| WO | WO 2004/018609 A1 | 3/2004 | |
| WO | WO 2004/026276 A1 | 4/2004 | |
| WO | WO 2004/050055 A1 | 6/2004 | |
| WO | WO 2005/067875 A1 | 7/2005 | |

OTHER PUBLICATIONS

XP002332779 "Olay Daily Renewal Moisturizing Body Wash" Online URL: http://householdprdoucts.nlm.nih.gov/cgi-bin/household.brands?tbl=brands&id=16003084.

* cited by examiner

STABLE, PATTERNED MULTI-PHASED PERSONAL CARE COMPOSITION

CROSS REFERENCE TO RELATED APPLICATIONS

This application claims the benefit of U.S. Provisional application Ser. No. 60/617,392 (Case 9791P), filed on Oct. 8, 2004, U.S. Provisional application Ser. No. 60/628,015 (Case 9834P), filed on Nov. 15, 2004, and U.S. Provisional application Ser. No. 60/680,113 (Case 9834P2), filed on May 12, 2005.

FIELD OF THE INVENTION

The present invention relates to a structured multi-phase personal care composition that preferably comprises at least one branched anionic surfactant.

BACKGROUND OF THE INVENTION

Personal care compositions are well known and widely used. Desirable personal care composition must meet a number of criteria. For example, in order to be acceptable to consumers, a personal care composition must exhibit good cleaning properties, must exhibit good lathering characteristics, must be mild to the skin (not cause drying or irritation) and preferably should even provide a conditioning benefit to the skin. Multi-phase personal cleansing compositions provide such benefits and can be made with a combination of structured surfactant phase and a benefit phase for moisturization. These types of multi-phase compositions can even be visually distinct.

It is desired to produce visually distinct compositions that are mild, and stable at a reasonable cost to the consumer. One method of producing mild compositions that are cost effective would be to minimize the surfactant level. Another method to produce a mild composition is to add a hydrophobic benefit phase. Very mild, personal care compositions can be prepared with the combination of low surfactant level and the presence of a hydrophobic benefit phase. However, minimizing surfactant level can cause instability in the surfactant phase which can be further exacerbated by adding hydrophobic benefit agents leading to loss of structure. Moreover, the lather volume of the personal care composition is reduced due to the combination of less surfactant and the presence of a hydrophobic component. Thus, it is difficult to create a mild, stable, high lathering personal cleansing composition with a low surfactant level in the presence of a hydrophobic benefit phase.

Accordingly, the need still remains for a structured multi-phase personal care composition that provides cleansing with increased lather longevity and improved lathering characteristics, and skin benefits such as improved clinical dry skin, silky skin feel, improved soft skin feel, and improved smooth skin feel with low levels of surfactants present in the composition.

SUMMARY OF THE INVENTION

The present invention is a structured multi-phase personal care composition that comprises a first visually distinct structured phase that comprises a cleansing phase and a second visually distinct phase. The cleansing phase comprises from about 2 to about 23.5% by weight of the cleansing phase of surfactant component. Preferably, the surfactant component comprises at least one branched anionic surfactant. Preferably, the branched anioinic surfactant comprises monomethyl branched surfactant.

It is known that anionic surfactants in personal cleansing compositions are used to generate lather volume, structure, and tendency to mildness or harshness. It is therefore desirable to select anionic surfactants that can be used at reduced levels and yet have the same amount of stable structure in the presence of hydrophobic benefit agents, and lather volume. The inventors believe that the use of branched anionic sulfate in personal care compositions allow structure, stability and lather volume to be attained at lower surfactant levels, promoting mildness on the skin, and at reasonably costs to the user. Some preferred surfactant components comprise a substantial level of monomethyl branched anionic surfactants leading to mildness, lather, structure and stability of structure in the presence of a hydrophobic benefit phase. Other preferred surfactants comprise a substantial level of anionic surfactants having other types of branching, leading to mildness, lather, structure and stability of structure in the presence of a hydrophobic benefit phase. Still other preferred surfactants comprise mixtures of branched and linear anionic surfactants, and mixtures of anionic surfactants with co-surfactants, providing an optimal balance of properties.

DETAILED DESCRIPTION OF THE INVENTION

The term "ambient conditions" as used herein, refers to surrounding conditions at one (1) atmosphere of pressure, 50% relative humidity, and 25° C.

By the term "multi-phase" or "multi-phase" as used herein, is meant that the phases of the present compositions occupy separate but distinct physical spaces inside the package in which they are stored, but are in direct contact with one another (i.e., they are not separated by a barrier and they are not emulsified or mixed to any significant degree). In one preferred embodiment of the present invention, the "multi-phase" personal care compositions comprise at least two visually distinct phases which are present within the container as a visually distinct pattern. The pattern results from the combination of the "multi-phase" composition by a process herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof.

In a preferred embodiment, the striped pattern may be relatively uniform across the dimension of the package. Alternatively, the striped pattern may be uneven, i.e. wavy, or may be non-uniform in dimension. The striped pattern does not need to necessarily extend across the entire dimension of the package. The size of the stripes can be at least about 0.1 mm in width and 10 mm in length, preferably at least about 1 mm in width and at least 20 mm in length as measured from the package exterior. The phases may be various different colors, and/or include particles, glitter or pearlescent agents in at least one of the phases in order to offset its appearance from the other phase(s) present.

The term "multi-phase personal care composition" as used herein, refers to compositions intended for topical application to the skin or hair.

The term "stable" as used herein, unless otherwise specified, refers to compositions that maintain at least two "separate" phases when sitting in undisturbed physical contact at ambient conditions for a period of at least about 180 days wherein the distribution of the two phases in different locations in the package does not significantly change over time. Compositions of the present invention, preferably exhibit enhanced stability according to the T-Bar method disclosed herein.

The term "structured," as used herein means having a rheology that confers stability on the multi-phase composition. The degree of structure is determined by the Yield Stress and Zero Shear Viscosity Method and by the Ultracentrifugation Method, both described hereafter. When a phase is a structured phase, typically it has a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter. When a phase is a structured phase, it may also typically have a Zero Shear Viscosity of at least about 500 Pascal-seconds (Pa-s), preferably at least about 1,000 Pa-s, more preferably at least about 1,500 Pa-s, even more preferably at least about 2,000 Pa-s. Accordingly, when a cleansing phase or a surfactant phase of the multi-phase composition of the present invention is structured, it has a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized. The term "visually distinct phase" as used herein, refers to a region of the multi-phase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase may also be constituted or re-constituted, collected, or separated into a bulk phase in order to observe its properties, e.g., by centrifugation, filtration or the like.

Product Form:

The multi-phase personal care composition of the present invention is typically extrudable or dispensible from a package. The multi-phase personal care compositions typically exhibit a viscosity of from about 1,500 centipoise (cP) to about 1,000,000 cP, as measured by the Viscosity Method as described in copending application Ser. No. 10/841174 filed on May 7, 2004 titled "Mulit-phase Personal Care Compositions."

When evaluating a structured multi-phase personal care composition, by the methods described herein, preferably each individual phase is evaluated prior to combining, unless otherwise indicated in the individual methodology. However, if the phases are combined, each phase can be separated by centrifugation, ultracentrifugation, pipetting, filtering, washing, dilution, concentration, or combination thereof, and then the separate components or phases can be evaluated. Preferably, the separation means is chosen so that the resulting separated components being evaluated is not destroyed, but is representative of the component as it exists in the structured multi-phase personal care composition, i.e., its composition and distribution of components therein is not substantially altered by the separation means. Generally, multi-phase compositions comprise domains significantly larger than colloidal dimensions so that separation of the phases into the bulk is relatively easy to accomplish while retaining the colloidal or microscopic distribution of components therein. Preferably, the compositions of the present invention are rinse-off formulations, by which is meant the product is applied topically to the skin or hair and then subsequently (i.e., within minutes) the skin or hair is rinsed with water, or otherwise wiped off using a substrate or other suitable removal means with deposition of a portion of the composition.

In a preferred embodiment of the present invention the structured multi-phase personal care composition comprises at least two visually distinct phases wherein a first phase is visually distinct from a second phase. Preferably, the visually distinct phases are packaged in physical contact with one another and are stable. Preferably, the visually distinct phases form a pattern.

Phases:

The multi-phase personal care compositions of the present invention comprise at least two visually distinct phases, wherein the composition can have a first structured phase, a second phase, a third phase, a fourth phase and so on. The ratio of a first phase to a second phase is preferably from about 1:99 to about 99:1, preferably from about 90:10 to about 10:90, more preferably from about 80:20 to about 20:80, even more preferably from about 70:30 to about 30:70, still even more preferably from about 60:40 to about 40:60, even still even more preferably about 50:50. Each phase could be one or more of the following nonlimiting examples including: a cleansing phase, a benefit phase, and a non-lathering structured aqueous phase, which are described in greater detail hereinafter. When a cleansing phase is present with a second phase the ratio of the cleansing phase to the second phase, by volume of the phases, is typically from about 99:1 to about 1:99, preferably from about, 90:10 to about 10:90, more preferably from about 80:20 to about 20:80, even more preferably from about 70:30 to about 30:70, still even more preferably from about 50:50.

Cleansing Phase:

The multi-phase personal care composition of the present invention can comprise a cleansing phase. The cleansing phase preferably comprises at least one branched anionic surfactant. Preferably, the surfactant component comprises a mixture of surfactants. The structured multi-phase personal care composition typically comprises from about 1% to about 99%, by weight of the composition, of said cleansing phase.

Surfactant Component:

The surfactant component preferably comprises a lathering surfactant or a mixture of lathering surfactants. The surfactant component preferably comprises at least one branched anionic surfactant. The surfactant component comprises surfactants suitable for application to the skin or hair. Suitable surfactants for use herein include any known or otherwise effective cleansing surfactant suitable for application to the skin, and which are otherwise compatible with the other essential ingredients in the structured multi-phase personal care composition including water. These surfactants include anionic, nonionic, cationic, zwitterionic, amphoteric surfactants, soap, or combinations thereof. Preferably, anionic surfactant comprises at least 40% of the surfactant component, more preferably from about 45% to about 95% of the surfactant component, even more preferably from about 50% to about 90%, still more preferably from about 55% to about 85%, and even still most preferably at least about 60% of the surfactant component comprises anionic surfactant.

The multi-phase personal care composition preferably comprises a surfactant component at concentrations ranging from about 2% to about 23.5%, more preferably from about 3% to about 21%, even more preferably from about 4% to about 20.4%, still more preferably from about 5% to about 20%, still even more preferably from about 13% to about 18.5%, and even still even more preferably from about 14% to about 18%, by weight of the cleansing phase.

The cleansing phase comprising the surfactant component is preferably a structured domain comprising surfactants. The structured domain enables the incorporation of high levels of benefit components in a separate phase that are not emulsified in the composition. In a preferred embodiment the structured domain is an opaque structured domain. The opaque structured domain is preferably a lamellar phase. The lamellar phase produces a lamellar gel network. The lamellar phase can provide resistance to shear, adequate yield to suspend particles and droplets and at the same time provides long term stability, since it is thermodynamically stable. The lamellar phase tends to have a higher viscosity thus minimizing the need for viscosity modifiers.

The cleansing phase typically provides a Total Lather Volume of at least about 600 ml, preferably greater than about 800ml, more preferably greater than about 1000 ml, even more preferably greater than about 1200 ml, and still more preferably greater than about 1500 ml, as measured by the Lather Volume Test described hereafter. The cleansing phase preferably has a Flash Lather Volume of at least about 300 ml, preferably greater than about 400 ml, even more preferably greater than about 500 ml, as measured by the Lather Volume Test described hereafter.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975.

Non-limiting examples of anionic surfactants suitable for use in the surfactant component of the cleansing phase include alkyl and alkyl ether sulfates, alkyl sulfonates, alkyl carboxylates, and alkyl phosphates having an average of about 8 to about 24 carbon atoms. Preferred alkyl ether sulfates are the condensation products of ethylene oxide (EO) and a fatty alcohol, having an average of 0 (i.e. the sulfate) to about 15 moles of ethylene oxide per fatty alcohol. Specific examples of alkyl ether sulfates which may be used in the cleansing phase are sodium, potassium, TEA, DEA and ammonium salts of coconut alkyl triethylene glycol ether sulfate and tallow alkyl triethylene glycol ether sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles EO.

Preferred linear anionic surfactants for use in the surfactant component of the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, sodium cocoyl isethionate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof. Preferred branched anionic surfactants are described below.

Mixtures of anionic surfactants may be used in some embodiments, including mixtures of linear and branched surfactants, and anionic surfactants with nonionic, amphoteric, and/or zwitterionic surfactants.

Additional surfactant from the classes of amphoteric, zwitterionic, cationic, and/or nonionic surfactants may be incorporated in surfactant component of the cleansing phase.

Amphoacetates and diamphoacetates may also be used. Sodium lauroamphoacetate, sodium cocoamphoactetate, disodium lauroamphoacetate, and disodium cocodiamphoacetate are preferred in some embodiments.

Cationic surfactants can also be used in the cleansing phase, but are generally less preferred, and preferably represent less than about 5% by weight of the compositions.

Suitable nonionic surfactants for use in the aqueous cleansing phase include condensation products of alkylene oxide groups (hydrophilic in nature) with an organic hydrophobic compound, which may be aliphatic or alkyl aromatic in nature, and may contain a linear or a branched hydrocarbon portion.

In one embodiment of the present invention, the cleansing phase comprises a surfactant component comprising a mixture of at least one nonionic surfactant, at least one anionic surfactant and at least one amphoteric surfactant, and an electrolyte.

Branched Anionic Surfactants:

At least one anionic surfactant comprising anionic surfactant molecules of the present invention is preferably branched. A surfactant molecule is branched when the hydrocarbon tail of the surfactant molecule comprises at least one ternary or quaternary carbon atom, such that a methyl, ethyl, propyl, butyl, pentyl or hexyl side chain extends from the hydrocarbon backbone. The hydrocarbon backbone is described by the longest hydrocarbon length in the hydrocarbon tail. A side chain in the branched hydrocarbon of a surfactant molecule can be described by its position on the backbone, counting from the first carbon attached to a hydrophilic atom, enumerated as carbon number 1, the adjacent carbon on the backbone being carbon number 2, and so on. Side chains are also described by their length, a single carbon side chain denoted methyl; a 2-carbon length denoted ethyl, and so on. Side chains that have their own branching are denoted by conventional nomenclature techniques, e.g., isopropyl, but are less common. Anionic surfactant molecules which do not have branching are linear anionic surfactant molecules, and surfactants comprising a preponderance of linear anioinic surfactant molecules as indicated hereafter are linear anionic surfactants. Most anionic surfactants derived from common natural sources such as coconut and palm, are linear anionic surfactants, such as ammonium lauryl sulfate, sodium lauryl ether sulfate. Linear anionic surfactants can also be derived from other sources including synthetic.

Because an anionic surfactant typically comprises a mixture of different types of surfactant molecules, anionic surfactants can be called linear or branched depending on the relative amounts of individual surfactant molecules of different types that comprise the anionic surfactant. For example, sodium tridecyl sulfate and sodium trideceth sulfate can be called branched surfactants because they typically comprise nearly all (>95%) branched surfactant molecules. For the purposes of the present invention, an anionic surfactant is considered branched surfactant when at least 10% of its hydrocarbon chains are branched molecules.

Branched anionic surfactants comprise surfactant molecules having different kinds of branching. Some branched anionic surfactants, such as tridecanol based sulfates such as sodium trideceth sulfate, comprise a high level of branching, with over 80% of surfactant molecules comprising at least 2 branches and having an average of about 2.7 branches per molecule in some sodium trideceth sulfates. Other branched anionic surfactants, such as $C_{12-13}$ alkyl sulfate derived from Safol™ 23 alcohol (Sasol, Inc, Houston, Tex., USA) comprise a mixture of about 50-55% linear anionic surfactant molecules, with about 15-30% branched surfactant molecules. For the purposes of the present invention, anionic surfactants comprising more than 10% branched surfactant molecules, but having an average of less than 2.0 branches per molecule, are considered monomethyl branched anionic surfactants.

Branching information for many surfactants is typically known or obtainable from suppliers of branched alcohol feedstocks. For example, Sasol publishes the following information related to Safol™ 23 primary alcohol:

| | |
|---|---|
| Linear Alcohol Isomers | 50% |
| Mono-Methyl Alcohol Isomers | 30% |
| Other Primary Alcohol Isomers | <20% |
| Total | 100% |

Safol™ 23 alcohol can be sulfated, for example in an $SO_3$/air stream falling film reactor followed by rapid neutralization with sodium hydroxide to produce sodium $C_{12-13}$ alkyl sulfate, a process known in the art. Since the sulfation process involves no rearrangement of the hydrocarbon backbone, the backbone of the $C_{12-13}$ alkyl sulfate has the same structure as the Safol™ 23 alcohol, and is a branched anionic surfactant, and is also a monomethyl branched anionic surfactant. Other suppliers of alcohols provide similar information on their primary alcohols, e.g., Shell Chemical for the Neodol™ primary alcohols. In the absence of published analytical information by established methods from material suppliers on branching of a surfactant or its feedstock alcohol, analytical techniques known to those skilled in the art can be used to determine branching. For example, when the structure of the hydrocarbon tail is not very complex (i.e., less than about a dozen major components), a gas chromatography—mass spectrometry (GC-MS) technique can be used, involving oxidation of the alcohol in acetone (cosolvent) by a 3.3 M $H_2CrO_4$ Jones Reagent to a fatty acid followed by oxazoline derivatization using 2-amino, 2-methyl, 1-propanol at 200C for 2 hours, dilution with $CHCl_3$ and subsequent washing with distilled water, drying with sodium sulfate prior to injection into a split injection (280C) or on-column injection. A typical GC program is 80-320C at 5C/min rate on a 30 m×0.25 mm DB-1 (0.25 uM film) column, and can give specific information on branching location for a majority of a hydrocarbon tail of an anionic surfactant. When co-elution of species and/or elution of unknown components occur, GC-MS is able to obtain the amount of branched components, which is taken as 100% minus the sum of n-C12 and n-C13 eluted. Typically, $n-C_{11}$, $n-C_{12}$ and $n-C_{13}$ elution times are known for a column and/or can be obtained by simple running of standards which are available. By convention for our invention, inventors sum all oxazoline peaks in the GC window between $n-C_{11}$ and $n-C_{12}$, said peaks are the branched $C_{12}$ peaks; sum all oxazoline peaks in the GC window between $n-C_{12}$ and $n-C_{13}$, said peaks are the branched $C_{13}$ peaks; dividing the peak areas obtained by the total area obtained, including linear $C_{12}$ and linear $C_{13}$, to obtain the fractional amount of each component. By our convention, the sum of the peak fractions in the branched $C_{12}$ and branched $C_{13}$ windows, added together, is the fraction of branched molecules, which can be expressed as a percentage. The integrated area under each GC peak is the peak information used in the calculations. If necessary, the surfactant can even be obtained by extraction from a composition first, e.g. by filtration such as crossflow filtration. From the GC data, the number of branch points per hydrocarbon chain is summed, multiplying number of branches per molecule by mole fraction for each species identified to obtain an average degree of branching per molecule for the surfactant. For example, 50% of molecules having 1 branch point with 50% linear molecules is an average degree of branching of 0.5. For highly branched molecules (>1.25 average degree of branching), such as sodium trideceth sulfate, determining degree of branching from the GC spectra can be difficult and require specialized equipment, so instead is determined from conventional NMR techniques, using the ratio of ternary to secondary carbon-carbon bonds in the hydrocarbon tail to determine average degree of branching.

Branched anionic surfactants include but are not limited to the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, and sodium $C_{12-14}$ pareth-n sulfate. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Preferred alcohols are Safol™ 23 and Neodol™ 23. Preferred alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

Monomethyl branched anionic surfactants include but are not limited to the branched anionic sulfates derived from Safol™ 23-n and Neodol™ 23-n as previously described, where n is an integer between 1 and about 20. Fractional alkloxylation is also useful, for example by stoichiometrically adding only about 0.3 moles EO, or 1.5 moles EO, or 2.2 moles EO, based on the moles of alcohol present, since the molecular combinations that result are in fact always distributions of alkoxylates so that representation of n as an integer is merely an average representation. Preferred monomethyl branched anionic surfactants include a $C_{12-13}$ alkyl sulfate derived from the sulfation of Safol™ 23, which has about 28% branched anionic surfactant molecules; and a C12-13 pareth sulfate derived from Neodol™ 23-3, which has about 10-18% branched anionic surfactant molecules.

When the anionic surfactant is a branched anionic primary sulfate, it may contain some of the following branched anionic surfactant molecules: 4-methyl undecyl sulfate, 5-methyl undecyl sulfate, 7-methyl undecyl sulfate, 8-methyl undecyl sulfate, 7-methyl dodecyl sulfate, 8-methyl-dodecyl sulfate, 9-methyl dodecyl sulfate, 4,5-dimethyl decyl sulfate, 6,9-dimethyl decyl sulfate, 6,9-dimethyl undecyl sulfate, 5-methyl-8-ethyl undecyl sulfate, 9-methyl undecyl sulfate, 5,6,8-trimethyl decyl sulfate, 2-methyl dodecyl sulfate, and 2-methyl undecyl sulfate. When the anionic surfactant is a primary alkoxylated sulfate, these same molecules may be present as the n=0 unreacted alcohol sulfates, in addition to the typical alkoxylated adducts that result from alkoxylation (e.g., Neodol™ 23-3 mol EO retains typically 16% unreacted Neodol™ 23 with 57% of molecules having 1 to 5 EO molecules reacted, according to Shell Chemicals technical literature, "Typical Distributions of NEODOL Ethoxylate Adducts").

Non-Ionic Surfactant

In an alternate embodiment of the present invention, the multi-phase personal care composition can comprise at least one nonionic surfactant. Preferably the nonionic surfactant has an HLB from about 1.0 to about 15.0, preferably from about 3.4 to about 15.0, more preferably from about 3.4 to about 9.5, even more preferably from about 3.4 to about 5.0. The multi-phase personal care composition preferably comprises a nonionic surfactant at concentrations ranging from about 0.01% to about 50%, more preferably from about 0.10% to about 10%, and even more preferably from about 0.5% to about 5.0%, by weight of the surfactant component.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, alkanolamides, ethoxylated alcohols and mixtures thereof. In a preferred embodiment the nonionic surfactant is selected from the group consisting of glyceryl monohydroxystearate, steareth-2, isosteareth-2, hydroxy stearic acid, propylene glycol stearate, PEG-2 stearate, sorbitan monostearate, glyceryl stearate, glyceryl laurate, laureth-2, cocamide monoethanolamine, lauramide monoethanolamine, and mixtures thereof. In a preferred embodiment the nonionic surfactant is selected from steareth-2, laureth-2, and isosteareth-2.

Nonionic surfactants also useful herein include, lauramine oxide, cocoamine oxide.

Amphoteric and Zwitterionic Surfactants:

In the one embodiment of the present invention the multi-phase personal care composition can comprise at least one amphoteric surfactant. Amphoteric surfactants suitable for use in the cleansing phase include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, and N-alkyltaurines such as the one prepared by reacting dodecylamine with sodium isethionate according to the teaching of U.S. Pat. No. 2,658,072 issued to Kosmin, et al.

Zwitterionic surfactants suitable for use in the cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like, amidobetaines and amidosulfobetaines, wherein the $RCONH(CH_2)_3$ radical is attached to the nitrogen atom of the betaine are also useful in this invention.

Electrolyte:

The electrolyte, if used, can be added per se to the multi-phase personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate. A preferred electrolyte is sodium chloride. The electrolyte is preferably added to the surfactant component of the composition.

The electrolyte, when present, should be present in an amount which facilitates formation of the stable composition. Generally, this amount is from about 0. 1% to about 15% by weight, preferably from about 1% to about 6% by weight of the multi-phase personal care composition, but may be varied if required.

In another one embodiment of the present invention, the surfactant for use in the cleansing phase can be mixtures of surfactants. Suitable surfactant mixtures can comprise water, at least one anionic surfactant as described previously, an electrolyte as described previously, and at least one alkanolamide.

The amount of alkanolamide in the composition is typically from about 0.1% to about 10%, by weight of the cleansing phase, and in some embodiments is preferably from about 2% to about 5%, by weight of the cleansing phase.

Benefit Phase:

The multi-phase personal care compositions of the present invention can comprise a benefit phase. The benefit phase in the present invention is preferably anhydrous. The benefit phase typically comprises hydrophobic materials. The benefit phase comprises from about 1% to about 100%, preferably at least about 35%, most preferably at least about 50%, by weight of the benefit phase, of a hydrophobic material. The hydrophobic materials suitable for use in the present invention preferably have a Vaughan Solubility Parameter of from about 5 to about 15 $(cal/cm^3)^{1/2}$. The hydrophobic compositions are preferably selected among those having defined Theological properties as described hereinafter, including selected Consistency value (K) and Shear Index (n). These preferred rheological properties are especially useful in providing the multi-phase personal care compositions with improved deposition of hydrophobic materials.

Vaughan Solubility Parameter Value (VSP):

The benefit phase of the multi-phase personal care composition typically comprises hydrophobic materials having a Vaughan Solubility Parameter (VSP) of from about 5 to about 15 $(cal/cm^3)^{1/2}$, preferably from about 5 to about 10 $(cal/cm^3)^{1/2}$, more preferably from about 6 to about $9(cal/cm^3)^{1/2}$. These solubility parameters are well known in the formulation arts, and are defined by Vaughan in *Cosmetics and Toiletries*, Vol. 103.

Non-limiting examples of hydrophobic materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

Rheology:

Rheology is used to determine the preferred skin feel profile of the benefit phase so that when the structured multi-phase personal care composition is deposited on the skin, the skin feels moisturized but not heavy or sticky or draggy. A measure of the skin feel of the benefit phase can be defined by Consistency Value (K) and Shear Index (n). The benefit phase has a Consistency Value (K) from about 20 to about 2,000 Pa-s, preferably from about 25 to about 500 Pa-s, more preferably from about 30 to about 450 Pa-s, still more preferably from about 30 to about 400 Pa-s and even still more preferably from about 30 to about 350 Pa-s. The benefit phase has a Shear Index from about 0.025 to about 0.99, preferably from about 0.05 to about 0.70 and more preferably from about 0.09 to about 0.60. The values are determined at 25° C. in the Test Methods Section below.

The benefit phase can be characterized by Consistency Value (K) and Shear Index (n) values as defined by the above-described ranges, wherein these defined ranges are selected to provide reduced stickiness during and after application of the multi-phase personal care composition on hair or skin.

Nonlimiting examples of hydrophobic material suitable for use herein can include a variety of hydrocarbons, oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, polyglycerin fatty acid esters, lanolin and its derivatives, wax esters, beeswax derivatives, sterols and phospholipids, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, and combinations thereof.

Non-limiting examples of silicone oils suitable for use as hydrophobic materials herein include dimethicone copolyol, dimethylpolysiloxane, diethylpolysiloxane, mixed $C_1$-$C_{30}$ alkyl polysiloxanes, phenyl dimethicone, dimethiconol, and combinations thereof. Preferred are non-volatile silicones selected from dimethicone, dimethiconol, mixed $C_1$-$C_{30}$ alkyl polysiloxane, and combinations thereof. Nonlimiting examples of silicone oils useful herein are described in U.S. Pat. No. 5,011,681 issued to Ciotti et al.

Non-limiting examples of diglycerides and triglycerides suitable for use as hydrophobic materials herein include castor oil, soy bean oil, derivatized soybean oils such as maleated soy bean oil, safflower oil, corn oil, almond oil, palm oil and sesame oil, vegetable oils and derivatives, sunflower seed oil, coconut oil and derivatizes, cottonseed oil and derivatized cottonseed oil, jojoba oil, cocoa butter, and combinations thereof.

Non-limiting examples of alkyl esters suitable for use as hydrophobic materials herein include isopropyl esters of fatty acids and long chain esters of long chain (i.e. $C_{10}$-$C_{24}$) fatty acids, e.g. cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, and combinations thereof.

Non-limiting examples of alkenyl esters suitable for use as hydrophobic materials herein include oleyl myristate, oleyl stearate, oleyl oleate, and combinations thereof.

Non-limiting examples of polyglycerin fatty acid esters suitable for use as hydrophobic materials herein include, decaglyceryl diisostearate, decaglyceryl monolaurate, hexaglyceryl monooleate, and combinations thereof.

Non-limiting examples of lanolin and lanolin derivatives suitable for use as hydrophobic materials herein include lanolin oils, waxes, esters and combinations thereof.

Still other suitable hydrophobic materials include wax esters, non-limiting examples of which include beeswax and its derivatives, spermaceti, and combinations thereof. Also useful are vegetable waxes such as carnauba and candelilla waxes; sterols such as cholesterol, and combinations thereof.

The benefit phase of the composition preferably can comprise one or more hydrophobic materials, wherein at least 1% by weight of the hydrophobic materials are selected from petrolatum, mineral oil, sunflower seed oil, alkyl siloxanes, polymethylsiloxanes and methylphenylpolysiloxanes, and combinations thereof. More preferably, at least about 20% by weight of the hydrophobic materials are selected from the groups of petrolatum, mineral oil, paraffins, polyethylene, polydecene, dimethicones, alkyl siloxanes, lanolins. More preferably, at least about 50% by weight of the hydrophobic materials are selected from the groups of petrolatum, mineral oil, paraffins, polyethylene, polydecene, dimethicones, alkyl siloxanes, lanolins.

Structured Aqueous Phase:

The multi-phase personal care compositions of the present invention can comprise a structured aqueous phase. The structured aqueous phase of the composition comprises a water structurant and water. The structured aqueous phase can be hydrophilic and in a preferred embodiment the structured aqueous phase is a hydrophilic, non-lathering gelled water phase. In addition, the structured aqueous phase typically comprises less than about 5%, preferably less than about 3%, and more preferably less than about 1%, by weight of the structured aqueous phase, of a surfactant. In one embodiment of the present invention, the structured aqueous phase is free of lathering surfactant in the formulation.

The structured aqueous phase of the present invention can comprise from about 30% to about 99%, by weight of the structured aqueous phase, of water. The structured aqueous phase generally comprises more than about 50%, preferably more than about 60%, even more preferably more than about 70%, still more preferably more than about 80%, by weight of the structured aqueous phase, of water.

The structured aqueous phase will typically have a pH of from about 5 to about 9.5, more preferably about 7. The structured aqueous phase can optionally comprise a pH regulator to facilitate the proper pH range.

A water structurant for the structured aqueous phase can have a net cationic charge, net anionic charge, or neutral charge.

The structured aqueous phase of the present compositions can further comprise optional ingredients such as those described hereinafter. Preferred optional ingredients for the structured aqueous phase include pigments, pH regulators, and preservatives. In one embodiment, the structured aqueous phase comprises a water structurant, water, a pH regulator (e.g. triethanolamine), and a preservative.

Water Structurant:

The structured aqueous phase can comprise from about 0.1% to about 30%, preferably from about 0.5% to about 20%, more preferably from about 0.5% to about 10%, and even more preferably from about 0.5% to about 5%, by weight of the structured aqueous phase, of a water structurant.

The water structurant is typically selected from the group consisting of inorganic water structurants, charged polymeric water structurants, water soluble polymeric structurants, associative water structurants, and mixtures thereof.

Non-limiting examples of inorganic water structurants for use in the multi-phase personal care composition include silicas, polymeric gellants such as polyacrylates, polyacrylamides, starches, modified starches, crosslinked polymeric gellants, copolymers, and mixtures thereof.

Non-limiting examples of charged polymeric water structurants for use in the multi-phase personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), and mixtures thereof.

Non-limiting examples of water soluble polymeric structurants for use in the multi-phase personal care composition include cellulose gums and gel, and starches.

Non-limiting examples of associative water structurants for use in the multi-phase personal care composition include xanthum gum, gellum gum, pectins, alginates such as propylene glycol alginate, and mixtures thereof.

Additional Ingredients:

Polymeric Phase Structurant:

The phases of the multi-phase personal care composition, preferably the cleansing phase, can further comprise a polymeric phase structurant. The compositions of the present invention typically can comprise from about 0.05% to about 10%, preferably from about 0.1% to about 4% and more preferably from about 0.2% to about 2% by weight of the phase, of a polymeric phase structurant. Non-limiting examples of polymeric phase structurant include but is not limited to the following examples: deflocculating polymers, naturally derived polymers, synthetic polymers, crosslinked polymers, block polymers, block copolymers, copolymers, hydrophilic polymers, nonionic polymers, anionic polymers, hydrophobic polymers, hydrophobically modified polymers, associative polymers, oligomers, and copolymers thereof.

The polymeric phase structurant may also beneficially act in conjunction with other components of a cleansing phase or benefit phase or non-lathering structured aqueous phase, for example to form a distinct polymer rich sub-phase in the cleansing or benefit phase to enhance stability of the composition, improve mildness of the composition, increase deposition from the composition onto the skin. Such phases can broadly be considered coacervates and/or flocs, especially if they form upon dilution of the composition or the cleansing phase, and are observable by simple dilution and observation, such as a 5-10% dilution of the cleansing phase in water which can be centrifuged lightly. Coacervates can comprise polymer-surfactant interactions.

Preferably the polymeric phase structurant comprises a first monomer and a second monomer, wherein the first monomer is selected from the group consisting of acrylic acid, salts of acrylic acid, $C_1$-$C_4$ alkyl-substituted acrylic acid, salts of $C_1$-$C_4$ alkyl-substituted acrylic acid, $C_1$-$C_4$ alkyl esters of acrylic acid, $C_1$-$C_4$ alkyl esters of $C_1$-$C_4$ alkyl-substituted acrylic acid, maleic anhydride, and mixtures thereof; and the monomer is a long chain ester monomer selected from the group consisting of $C_{10}$-$C_{30}$ alkyl esters of acrylic acid, $C_{10}$-$C_{30}$ alkyl esters of $C_1$-$C_4$ alkyl-substituted acrylic acid, and mixtures thereof. The salts of the acids described in the previous sentence are selected from the group consisting of alkali metal salts, alkaline metal salts, ammonium salts, and mono-, di-, tri-, and tetra-alkyl ammonium salts. The $C_1$-$C_4$ alkyl-substituted acrylic acids described in the first sentence of this paragraph include methacrylic acids, ethacrylic acids, and the like, wherein the alkyl substituent can be either on the $C_2$ or $C_3$ position of the acid molecule. The $C_1$-$C_4$ alkyl esters described in the first sentence in this paragraph include methyl and ethyl esters as well as branched $C_3$ and $C_4$ esters.

Preferably the polymeric phase structurant can be crosslinked and further comprise a crosslinking. These polymeric phase structurant useful in the present invention are more fully described in U.S. Pat. No. 5,087,445, to Haffey et al., issued Feb. 11, 1992; U.S. Pat. No. 4,509,949, to Huang et al., issued Apr. 5, 1985, U.S. Pat. No. 2,798,053, to Brown, issued Jul. 2, 1957. See also, CTFA International Cosmetic Ingredient Dictionary, fourth edition, 1991, pp. 12 and 80.

Specific examples of naturally derived polymers which can be used in the cleansing or benefit phase are starch and starch derivates such as amylose and amylopectin, starch hydroxypropylphosphate, strach octenyl succinate; marine gums such as alginates and algin derivatives such as propylene glycol alginate; pectins such as high methoxy pectin; food and plant gums such as carageenans, gum arabic or acacia gums, guar gum, locust bean gum; biosaccharides such as xanthan gum; shellfish saccharides such as chitosan and its derivates; cellulose derivatives such as methylcellulose, ethylcellulose, hydroxypropylcellulose, hydroxyethylcellulose and other cellulose derivatives; gelatin, casein and other proteins.

Non-limiting examples of hydrophilic polymers which can be used in the cleansing or benefit phase are starches, celluloses, polyacrylates including the crosslinked polyacrylates, polyacrylamides including crosslinked polyacrylamides, xanthan gum and copolymers, associative thickeners such as acrylates/beheneth-25 methacrylate copolymer.

Liquid Crystalline Phase Inducing Structurant:

The phase of the present compositions, preferably the cleansing phase, optionally can further comprise a liquid crystalline phase inducing structurant, which when present is at concentrations ranging from about 0.3% to about 15%, by weight of the phase, more preferably at from about 0.5% to about 5% by weight of the phase. Not being bound by theory, the liquid crystalline phase inducing structurant functions in the compositions to form a thermodynamic domain, preferably a lamellar (structured) domain. It is believed the lamellar domain enhances the interfacial stability between the phases of the present compositions.

Suitable liquid crystalline phase inducing structurants include fatty acids or ester derivatives thereof, fatty alcohols, trihydroxystearin (available from Rheox, Inc. under the trade name THIXCIN® R). Nonlimiting examples of fatty acids which may be used are $C_{10}$-$C_{22}$ acids such as the following: lauric acid, oleic acid, isostearic acid, linoleic acid, linolenic acid, ricinoleic acid, elaidic acid, arichidonic acid, myristoleic acid and palmitoleic acid, and the like. Ester derivatives include propylene glycol isostearate, propylene glycol oleate, glyceryl isostearate, glyceryl oleate, propylene glycol dilaurate and polyglyceryl diisostearate, lauryl behenate and the like. Preferably, the liquid crystalline phase inducing structurant is selected from lauric acid, trihydroxystearin, lauryl pyrrolidone, and tridecanol.

Organic Cationic Deposition Polymer:

The structured multi-phase personal care compositions of the present invention can additionally comprise an organic cationic deposition polymer in the one or more phases as a deposition aid for the benefit agents described herein. Suitable cationic deposition polymers for use in the structured multi-phase personal care compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the structured multi-phase personal care composition. Suitable cationic deposition polymers that would be useful in the compositions of the present invention are disclosed in the co-pending and commonly assigned U.S. Patent Application Ser. No. 60/628,036 filed on Nov. 15, 2003 by Wagner, et al titled "Depositable Solids."

Nonlimiting examples of cationic deposition polymers for use in the structured multi-phase personal care compositions include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquatemium 10 which are available from Amerchol Corp. (Edison, N.J., USA) in their Polymer KG, JR and LR series of polymers with the most preferred being KG-30M.

Any anionic counterions can be associated with the cationic deposition polymers so long as the polymers remain soluble in water, in the structured multi-phase personal care compositions, or in a coacervate phase of the structured multi-phase personal care compositions, and so long as the counterions are physically and chemically compatible with the essential components of the structured multi-phase personal care composition or do not otherwise unduly impair product performance, stability or aesthetics. Nonlimiting examples of such counterions include halides (e.g., chlorine, fluorine, bromine, iodine), sulfate and methlylsulfate.

Particles:

The structured multi-phase personal care composition of the present invention can comprise a particle. A water insoluble particle of various shapes and densities is useful. In a preferred embodiment, the particle tends to have a spherical, an oval, an irregular, or any other shape in which the ratio of the largest dimension to the smallest dimension (defined as the Aspect Ratio) is less than about 10, preferably less than about 8, and still more preferably the Aspect Ratio of the particle is less than about 5. Preferably, the particle will also have physical properties which are not significantly affected by typical processing of the composition.

Exfoliant Particles:

The structured multi-phase personal care composition of the present invention can comprise an exfoliant particle. A preferred particle is selected from the group consisting of polyethylene, microcrystalline wax, jojoba esters, amourphors silica, talc, tracalcium orthophosphate, or blends thereof, and the like in at least one phase of the multi-phase personal care composition. The exfoliant particle is preferably present at a level of less than about 10%, by weight of the composition.

Shiny Particles:

The structured multi-phase personal care compositions of the present invention can comprise a shiny particle in at least one phase of the multi-phase personal care composition. Nonlimiting examples of shiny particles include the following: interference pigment, multi-layered pigment, metallic particle, solid and liquid crystals, and combinations thereof. An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. When pigment is applied and rinsed as described in the Pigment Deposition Tape Strip Method as described in copending application Ser. No. 60/469,075, filed on May 8, 2003, the deposited pigment on the skin is preferably at least 0.5 $\mu g/cm^2$, more preferably at least 1 $\mu g/cm^2$, and even more preferably at least 5 $\mu g/cm^2$. Interference pigments that are suitable for use in the compositions of the present invention are those disclosed in U.S. Pat. No. 6,395,691 issued to Liang Sheng Tsaur on May 28, 2002, U.S. Pat. No. 6,645,511 issued to Aronson, et al., U.S. Pat. No. 6,759,376 issued to Zhang, et al on Jul. 6, 2004, U.S. Pat. No. 6,780,826 issued on Aug. 24, 2004, U.S. Patent Application No. 2003/0054019 filed on May 21, 2002, published on Mar. 21, 2003 to Aronson, et al, as well as those pending and commonly assigned under U.S. Patent Application No. 60/469,570 filed on May 9, 2003 by Clapp, et al titled "Personal Care Compositions That Deposit Shiny Particles," and U.S. Patent Application No. 60/515,029 filed on Oct. 28, 2003, 2003 by Clapp, et al titled "Methods for Using Personal Care Compositions Containing Shiny Particles."

A portion of the interference pigment surface can be coated with a hydrophobic material. Hydrophobically modified interference pigments that are suitable for use in the compositions of the present invention are those disclosed in pending and commonly assigned under U.S. patent application Ser. No. 10/841,173 filed on May 7, 2004 by Clapp, et al titled "Personal Care Compositions Containing Hydrophobically Modified Interference Pigments."

Skin Lightening Agents:

The structured multi-phase personal care composition of the present invention can comprise a skin lightening agent.

Beads: The structured multi-phase personal care composition of the present invention can comprise beads. The beads may be any color and may be located in one phase or multiple phases of the of the multi-phase personal care composition. Suitable beads include those known in the art, including soft and hard beads. Suitable examples of soft beads include unispheres, made by Induchem, Unispheres NT-2806 (Pink). Suitable examples of hard beads include polyethylene or oxidized polyethylene, preferably those made by Accutech.

Optional Ingredients:

The structured multi-phase personal care composition can comprise a variety of additional optional ingredients. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention, including each phase as described herein.

Non-limiting optional ingredients include humectants and solutes. A preferred humectant is glycerin. Other usefulwater soluble, organic materials is selected from the group consisting of polyols, $C_2$-$C_{10}$ alkane diols, guanidine, glycolic acid and glycolate salts (e.g. ammonium and quaternary alkyl ammonium), lactic acid and lactate salts (e.g. ammonium and quaternary alkyl ammonium), polyhydroxy alcohols such as sorbitol, glycerol, hexanetriol, propylene glycol, hexylene glycol and the like, polyethylene glycol, sugars and starches, sugar and starch derivatives (e.g. alkoxylated glucose), panthenol (including D-, L-, and the D,L-forms), pyrrolidone carboxylic acid, hyaluronic acid, lactamide monoethanolamine, acetamide monoethanolamine, urea, and ethanol amines.

Nonionic polyethylene/polypropylene glycol polymers can be used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-SM wherein x equals 2 and n has an average value of about 5; PEG-7M wherein x equals 2 and n has an average value of about 7; PEG-9M wherein x equals 2 and n has an average value of about 9; PEG-14 M wherein x equals 2 and n has an average value of about 14; and PEG-90M wherein x equals 2 and n has an average value of about 90,000.

Other non limiting examples of these optional ingredients include vitamins and derivatives thereof (e.g., ascorbic acid, vitamin E, tocopheryl acetate, and the like), sunscreens; thickening agents (e.g., polyol alkoxy ester, available as Crothix from Croda), preservatives for maintaining the anti microbial integrity of the cleansing compositions, anti-acne medicants (resorcinol, salicylic acid, and the like), antioxidants, skin soothing and healing agents such as aloe vera extract, allantoin and the like, chelators and sequestrants, and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

The preferred pH range of the structured multi-phase personal care composition is from about 5 to about 8.

Test Methods:

Yield Stress and Zero Shear Viscosity Method:

The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 5 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m * \text{Log(stress)} + b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a %variation at each point, using Equation (2).

$$\% \text{ variation} = 100 * (\text{measured strain} - \text{predicted strain}) / \text{measured strain} \quad (2)$$

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Lather Volume Test:

Lather volume of a cleansing phase, a surfactant component or a structured domain of a structured multi-phase personal care composition, is measured using a graduated cylinder and a rotating apparatus. A 1,000 ml graduated cylinder is used which is marked in 10 ml increments and has a height of 14.5 inches at the 1,000 ml mark from the inside of its base (for example, Pyrex No. 2982). Distilled water (100 grams at 25° C.) is added to the graduated cylinder. The cylinder is clamped in a rotating device, which clamps the cylinder with an axis of rotation that transects the center of the graduated cylinder. Inject 0.50 grams of a surfactant component or cleansing phase from a syringe (weigh to ensure proper dosing) into the graduated cylinder onto the side of the cylinder, above the water line, and cap the cylinder. When the sample is evaluated, use only 0.25 cc, keeping everything else the same. The cylinder is rotated for 20 complete revolutions at a rate of about 10 revolutions per 18 seconds, and stopped in a vertical position to complete the first rotation sequence. A timer is set to allow 15 seconds for lather generated to drain. After 15 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells which comprise the lather ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum lather height is 1,000 ml (even if the total lather height exceeds the 1,000 ml mark on the graduated cylinder). 30 seconds after the first rotation is completed, a second rotation sequence is commenced which is identical in speed and duration to the first rotation sequence. The second lather volume is recorded in the same manner as the first, after the same 15 seconds of drainage time. A third sequence is completed and the third lather volume is measured in the same manner, with the same pause between each for drainage and taking the measurement.

The lather results after each sequence are added together and the Total Lather Volume determined as the sum of the three measurements, in milliters ("ml"). The Flash Lather Volume is the result after the first rotation sequence only, in ml, i.e., the first lather volume. Compositions according to the present invention perform significantly better in this test than similar compositions in conventional emulsion form.

Ultracentrifugation Method:

The Ultracentrifugation Method is used to determine the percent of a structured domain or an opaque structured domain that is present in a structured multi-phase personal care composition that comprises a cleansing phase comprising a surfactant component. The method involves the separation of the composition by ultracentrifugation into separate but distinguishable layers. The structured multi-phase personal care composition of the present invention can have multiple distinguishable layers, for example a non-structured surfactant layer, a structured surfactant layer, and a benefit layer.

First, dispense about 4 grams of multi-phase personal care composition into Beckman Centrifuge Tube (11×60 mm). Next, place the centrifuge tubes in an Ultracentrifuge (Beckman Model L8-M or equivalent) and ultracentrifuge using the following conditions: 50,000 rpm, 18 hours, and 25° C.

After ultracentrifuging for 18 hours, determine the relative phase volume by measuring the height of each layer visually using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$$H_s = H_a - H_b$$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows:

$$\text{Structured Domain Volume Ratio} = H_c/H_s * 100\%$$

If there is no benefit phase present, use the total height as the surfactant layer height, $H_s = H_a$.

The Shear Index (n) and Consistency Value (K):

The Shear Index (n) and Consistency Value (K) are known and accepted means for reporting the viscosity profile of materials having a viscosity that varies with applied shear rate using a Power Law model. The term "Consistency value" or "K" as used herein is a measure of viscosity and is used in combination with Shear Index, to define viscosity for materials whose viscosity is a function of shear rate. The measurements of Consistency value and Shear Index are made at 25° C. The units for "Consistency value" or "K" are Pascal seconds. The units for "Shear Index" are dimensionless.

Viscosity of a phase can be measured by applying a shear stress and measuring the shear rate using a rheometer, such as a TA Instruments AR2000 (TA Instruments, New Castle, Del., USA 19720). Viscosity is determined at different shear rates in the following manner. First, the benefit phase is obtained. If there exists more than one distinct (immiscible, e.g.) benefit phase in the composition, such as for example a silicone oil phase and a hydrocarbon phase, they are preferably prepared separately and/or separated from each other, and evaluated separately from each other, although certain benefit phases which are mixtures such as emulsions can be evaluated as mixtures, in addition to evaluating the individual benefit phases individually.

For measurement, a 40 mm diameter parallel plate geometry with a gap of 1 mm is used unless there are particles greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 1/seconds is obtained in the test, or the test is repeated with a fresh sample of the same component with a higher final stress value, maintaining the same rate of stress increase per time, until a shear rate of at least 500 1/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 1/sec shear rate, viscosity in Pa-s, shear rate in 1/sec, and using a least squares regression of the logarithm of viscosity vs. the logarithm of shear rate to obtain values of K and n according to the Power Law equation:

$$\mu = K(\gamma')^{(n-1)}$$

The value obtained for the log-log slope is (n-1) where n is the Shear Index and the value obtained for K is the Consistency Value, expressed in units of in Pa-s.

T-Bar Method for Assessing Structured Surfactant Stability In Presence of Lipid

The cleansing phase stability in the presence of lipid can be assessed using a T-Bar Viscosity Method. The apparatus for T-Bar measurement consists of a Brookfield DV-II+ Pro Viscometer with Helipath Accessory; Chuck, weight and closer assembly for T-bar attachment; T-bar Spindle D, a Personal Computer with Rheocalc software from Brookfield and a cable connecting the Brookfield Viscometer to the computer. First, weigh 40 grams of cleansing phase in a 4-oz glass jar. Centrifuge the jar at 2,000 rpm for 20 min to de-aerate the cleansing phase, which may also remove large particles by sedimentation or flotation. Measure the height of the cleansing phase $H_{surf}$ using an Electronic Caliper with a precision of 0.01 mm. Measure the initial T-bar viscosity by carefully dropping the T-Bar Spindle to the interior bottom of the jar and set the Helipath stand to travel in an upward direction. Open the Rheocalc software and set the following data acquisition parameters: set Speed to 5 rpm, set Time Wait for Torque to 00:01 (1 second), set Loop Start Count at 40. Start data acquisition and turn on the Helipath stand to travel upward at a speed of 22 mm/min. The initial T-Bar viscosity, $T_{ini}$, is the average T-Bar viscosity readings between the $6^{th}$ reading and the $35^{th}$ reading (the first five and the last five readings are not used for the average T-Bar viscosity calculation). Cap the jar and store at ambient temperature. Prepare a lipid blend by heating a vessel to 180° F. and add together 70 parts of Petrolatum (G2218 from WITCO) and 30 parts of Hydrobrite 1000 White Mineral Oil. Cool the vessel to 100° F. with slow agitation (200 rpm). Stop agitation and cool the vessel to ambient temperature overnight. Add 40 grams lipid blend (70/30 Pet/MO) to the jar containing the cleansing phase. Stir the cleansing phase and lipid together using a spatula for 5 min. Place the jar at 113° F. for 5 days. After 5 days, centrifuge the jar at 2000 rpm for 20 min (do not cool the jar first).

After centrifugation, cool down the jar and contents to ambient temperature, overnight. Observe the contents of the jar. A stable cleansing phase exhibits a uniform layer at the bottom of the jar, below the less dense petrolatum/oil phase. Unstable cleansing phase can form layers not present in the originally centrifuged cleansing phase (i.e., isotropic phase) either at the bottom or between the cleansing phase-lipid interface. If more than one layer is present in the cleansing phase, measure the height of each newly formed layer, $H_{new}$ using an Electronic Caliper. Add together the heights of all the newly formed layers. The new phase volume ratio is calculated as $H_{new}/H_{surf}*100\%$ using the height of all new layers added together as $H_{new}$. Preferably, a stable structured cleansing phase forms less than 10% of new phase volume. More preferably, a stable structured cleansing phase forms less than 5% of new phase volume. Most preferably, a stable structured cleansing phase forms 0% of new phase volume.

The T-Bar viscosity of the centrifuged contents of the jar is then measured using the T-Bar method above. Open the Rheocalc software and set the following data acquisition parameters: set Speed to 5 rpm, set Time Wait for Torque to 00:01 (1 second), set Loop Start Count at 80. Start the data acquisition and turn on the Helipath stand to travel upward at a speed of 22 mm/min. There is usually a distinctive viscosity jump between the cleansing phase layer and the lipid layer. The cleansing phase T-Bar viscosity after lipid exposure, $T_{aft}$, is the average reading between the $6^{th}$ T-Bar viscosity and the last T-Bar viscosity reading before the lipid jump. In the case where there is no distinctive T-Bar viscosity jump between cleansing phase and lipid phase, only use the average reading between the $6^{th}$ T-Bar viscosity reading and the $15^{th}$ reading as the average cleansing phase T-bar viscosity, $T_{aft}$. Preferably, a stable structured cleansing phase has $T_{aft}$ higher than 10,000 cP. More preferably, a stable structured cleansing phase has $T_{aft}$ higher than 15,000 cP. Most preferably, a stable structured cleansing phase has $T_{aft}$ higher than 20,000 cP.

Viscosity Retention is calculated as $T_{aft}/T_{ini}*100\%$. Preferably, a stable structured cleansing phase has >50% Viscosity Retention. More preferably, a stable structured cleansing phase has >70% Viscosity Retention. Most preferably, a stable structured cleansing phase has >80% Viscosity Retention.

Method of Use

The multi-phase personal care compositions of the present invention are preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The multi-phase personal care compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166 issued to Thibiant, et al. on Apr. 10, 2001. The method and apparatus allows two or more compositions to be filled with a spiral configuration into a single container. The method requires that at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. Specific non-limiting examples of such methods as they are applied to specific embodiments of the present invention are described in the following examples.

If the multi-phase personal care compositions contain patterns of varying colors it can be desirable to package these compositions in a transparent or translucent package such that the consumer can view the pattern through the package. Because of the viscosity of the subject compositions it may also be desirable to include instructions to the consumer to store the package upside down, on its cap to facilitate dispensing.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Examples 1 are comparative examples of the cleansing phase of the present invention. Examples 2-29 are examples of the present invention which can be used in multi-phase compositions of the present invention. Example 30 is a comparative example of the present invention. Examples 31-39 are examples of the cleansing phase with alternative polymeric structurants. Examples 40-41 are examples of structured aqueous phases. Examples 42-44 are examples of the benefit phase. The examples of the cleansing phase, structured aqueous phase and benefit phase can be combined using methods described herein.

Example 1 is a comparative example of a cleansing phase with a surfactant component that is outside the claimed ranges and which exhibits structure and stability at least in part due to its high level of surfactant, having a Yield Stress of 13.8 Pa. Example 30 is a comparative example of what typically happens is compositions with low 15 surfactant levels and does exhibit structure characteristic nor stability of the Examples of the present invention, in that Example 30 has a low a Zero Shear Viscosity of 900 Pa-s and T-Bar % Viscosity Change of −79% and 5% of a third phase.

| | Cleansing Phase Example: | | | | | | |
|---|---|---|---|---|---|---|---|
| | Comparative Example 1 | 2 | 3 | 4 | 5 | 6 | 7 |
| | Skin Benefit Components and Thickeners | | | | | | |
| Water, distilled | QS | QS | QS | QS | QS | QS | QS |
| Glycerin | 0.80 | 0.30 | 0.41 | 0.30 | 0.30 | 0.17 | 0.60 |
| Guar hydroxypropyl-trimonium chloride(N-Hance 3196, Aqualon Chem.) | 0.70 | 0.28 | 0.59 | 0.33 | 0.40 | 0.43 | 0.50 |
| PEG 90M (Polyox WSR 301, Amerchol Corp) | 0.20 | — | — | — | 0.10 | 0.05 | — |
| Citric acid | 0.40 | — | — | — | — | 0.46 | — |

-continued

| | | | | | | | |
|---|---|---|---|---|---|---|---|
| Surfactant Components | | | | | | | |
| Sodium trideceth sulfate (Cedepal TD-403, Stepan Co.) | — | — | — | — | — | 9.9 | — |
| ALS | — | 10.69 | 13.36 | 6.00 | 9.40 | — | — |
| SLS | — | — | — | — | — | — | 14.7 |
| Miracare SLB-365 (Rhodia, Inc.) (Sodium Trideceth Sulfate, Sodium Laurampho-acetate, Cocamide MEA) | 23.70 | — | — | 8.00 | — | — | — |
| Polyoxyethylene 2.5 lauryl alcohol (Arylpon F, Cognis Corp, Cincinnati, OH) | — | 2.37 | 2.96 | — | 2.10 | 1.3 | 3.26 |
| Cocamide monoethanolamine | — | — | — | 2.00 | — | — | — |
| Cocobetaine | — | 2.96 | 3.68 | — | 2.60 | 4.8 | 4.05 |
| Preservative and Minors | | | | | | | |
| Fragrance | 1.4 | 1.33 | 1.25 | 1.33 | 1.40 | 1.25 | 2.00 |
| Sodium chloride | 3.50 | 2.33 | 3.50 | 2.33 | 3.50 | 3.50 | 3.00 |
| Disodium EDTA | 0.05 | — | — | — | — | — | — |
| Preservative | 0.4 | 0.1 | 0.1 | 0.1 | 0.4 | 0.4 | 0.1 |
| Polymeric Phase Structurants | | | | | | | |
| Xanthan gum (Keltrol CGT from Kelco) | — | 0.33 | 0.33 | 0.33 | 0.26 | 0.50 | 0.35 |
| Acrylates/Vinyl Isodecanoate Crosspolymer (Stabylen 30 from 3V) | — | 0.67 | 0.53 | 0.67 | 0.54 | 0.50 | 0.35 |
| Final pH | 6.2 | 6.5 | 6.5 | 6.4 | 6.25 | 6.2 | 6.5 |
| surfactant component, % of cleansing phase | 23.7 | 16.0 | 20.0 | 16.0 | 14.1 | 16.0 | 22.0 |
| Anionic surfactant, % of surfactant component | 66 | 67 | 67 | 70 | 67 | 62 | 67 |
| Branched anionic surfactant, % of anionic surfactant | 100 | 0 | 0 | 33 | 0 | 100 | 0 |
| Monomethyl branched anionic surfactant, % of anionic | 0 | 0 | 0 | 0 | 0 | 0 | 0 |
| Zero shear viscosity, Pa-sec | 6530 | 7070 | 5630 | 2960 | 7550 | 8390 | 5200 |
| Yield stress, Pa | 13.8 | 17 | 18 | 16 | 23.6 | 4.1 | 25.6 |
| Coacervate | <1 mm | — | 4 ml | — | — | — | 6 ml |
| Lather Volume: Flash/Total (ml/ml) | 590/2080 | 460/1780 | 500/1860 | — | 470/1760 | — | 510/1930 |
| Structured Domain Volume Ratio, % | 88 | — | 86 | 86 | — | — | — |

| | Example: | | | | | | |
|---|---|---|---|---|---|---|---|
| | 8 | 9 | 10 | 11 | 12 | 13 | 14 |
| Skin Benefit Components and Thickeners | | | | | | | |
| Water, distilled | QS | QS | QS | QS | QS | QS | QS |
| Glycerin | — | — | 0.5 | 0.5 | 0.5 | 0.17 | 0.17 |
| NHance 3196, Aqualon | 0.49 | 0.45 | 0.45 | 0.45 | 0.45 | 0.43 | 0.43 |
| PEG 90M (WSR 301) | — | — | 0.08 | 0.08 | 0.08 | 0.05 | 0.05 |
| Citric acid | — | — | 0.2 | 0.2 | 0.2 | 0.46 | 0.46 |
| Surfactant Components | | | | | | | |
| Sodium trideceth sulfate (Cedepal TD-403) | — | — | — | — | — | 5.26 | — |
| ALS | — | — | — | — | — | 6.1 | 8.0 |
| AES | 14.1 | — | — | — | — | — | — |
| SLES (2 mol EO) | — | 15.1 | — | — | — | — | — |
| Miracare SLB-365 (Rhodia, Inc.) | — | — | 15.72 | 15.72 | 15.72 | — | 9.0 |
| Laureth 2 (Arylpon F) | 2.3 | 2.1 | — | — | — | 2.1 | — |
| Cocobetaine | 2.83 | 2.62 | — | — | — | 2.62 | 1.0 |
| Preservative and Minors | | | | | | | |
| Fragrance | 3.5 | 2.7 | 1.25 | 1.25 | 1.25 | 1.25 | 1.25 |
| Sodium chloride | 2.9 | 2.7 | 2.8 | 2.8 | 2.8 | 3.5 | 3.5 |
| Preservative | 0.1 | 0.1 | 0.25 | 0.25 | 0.25 | 0.3 | 0.3 |
| Polymeric Phase Structurants | | | | | | | |
| Xanthan (Keltrol CGT) | 0.83 | 0.59 | — | — | 0.5 | 0.5 | 0.5 |
| Stabylen 30, 3V | 1.08 | 0.68 | 0.5 | 0.8 | 0.5 | 0.5 | 0.5 |
| Final pH | 5.9 | 5.8 | 6.7 | 5.8 | 6.2 | 6.3 | 6.3 |
| Surfactant component, % of cleansing phase | 19.2 | 19.8 | 15.7 | 15.7 | 15.7 | 16.1 | 18.0 |
| Anionic surfactant, % of surfactant component | 73 | 77 | 66 | 66 | 66 | 71 | 77 |
| Branched anionic surfactant, % of anionic surfactant | 0 | 0 | 100 | 100 | 100 | 46 | 43 |
| Monomethyl branched anionic | 0 | 0 | 0 | 0 | 0 | 0 | 0 |

-continued

| | | | | | | | |
|---|---|---|---|---|---|---|---|
| surfactant, % of anionic surfactant | | | | | | | |
| Zero Shear Viscosity | 15800 | 1640 | 3330 | 8660 | 10100 | 12900 | 7110 |
| Yield Stress, Pa | 9.5 | 5.5 | 3.7 | 46 | 25.5 | 14 | 12 |
| Coacervate | — | — | — | — | 13 ml | — | — |
| Lather Volume: Flash/Total (ml/ml) | 400/1580 | 450/1750 | 490/1840 | 460/1800 | — | — | — |

| | Example: | | | | | |
|---|---|---|---|---|---|---|
| | 15 | 16 | 17 | 18 | 19 | 20 |
| Skin Benefit Components and Thickeners | | | | | | |
| Water, distilled | QS | QS | QS | QS | QS | QS |
| Glycerin | 0.5 | 0.5 | 0.5 | 0.5 | 0.3 | 0.43 |
| NHance 3196, Aqualon | 0.45 | 0.45 | 0.45 | 0.45 | 0.40 | 0.53 |
| PEG 90M (WSR 301) | 0.08 | 0.08 | 0.08 | 0.08 | 0.10 | 0.15 |
| Citric acid | 0.2 | 0.2 | 0.2 | 0.2 | — | 0.4 |
| Surfactant Components | | | | | | |
| Miracare SLB-365 (Rhodia) | 15.72 | 15.72 | 15.72 | 15.72 | — | 17.8 |
| Laureth 2 (Arylpon F, Cognis) | — | — | — | — | 3.0 | — |
| Cocobetaine | — | — | — | — | 3.7 | — |
| ALS | — | — | — | — | 13.4 | — |
| CMEA | — | — | — | — | — | 2.25 |
| Preservative and Minors | | | | | | |
| Fragrance | 1.25 | 1.25 | 1.25 | 1.25 | 1.4 | 1.5 |
| Sodium chloride | 2.8 | 2.8 | 2.8 | 2.8 | 3.5 | 3.4 |
| Disodium EDTA | — | — | — | — | 0.06 | 0.06 |
| Preservative | 0.25 | 0.25 | 0.25 | 0.25 | 0.39 | 0.4 |
| Triethanolamine | — | — | — | — | — | 0.38 |
| Titanium dioxide | — | — | — | — | — | 1.0 |
| Polymeric Phase Structurants | | | | | | |
| Xanthan (Keltrol CGT or 1000) | 0.3 | 0.3 | 0.3 | 0.3 | 0.13 | 0.25 |
| Carbomer (Carbopol 980) | 0.5 | — | — | — | — | — |
| Carbomer (Carbopol 954) | — | 0.5 | — | — | — | — |
| Carbomer (Carbopol 940) | — | — | 0.5 | — | — | — |
| Acrylates copolymer (Carbopol Aqua SF-1) | — | — | — | 0.5 | — | — |
| Stabylen 30 from 3V | — | — | — | — | 0.27 | 0.25 |
| Final pH | 6 | 6.1 | 6.1 | 6.4 | 6.25 | 6.2 |
| Surfactant component, % of cleansing phase | 15.7 | 15.7 | 15.7 | 15.7 | 20.1 | 20.1 |
| Anionic surfactant, % of surfactant component | 66 | 66 | 66 | 66 | 67 | 59 |
| Monomethyl branched anionic surfactant, % of anionic surfactant | 0 | 0 | 0 | 0 | 0 | 0 |
| Branched anionic surfactant, % of anionic surfactant | 100 | 100 | 100 | 100 | 0 | 100 |
| Zero Shear Viscosity | 5830 | 3930 | 6670 | 2810 | 8640 | — |
| Yield Stress, Pa | 2.4 | 4.1 | 2.6 | 16.6 | 13.8 | — |
| Lather Volume: Flash/Total (ml/ml) | — | 470/1830 | 400/1590 | — | 510/1850 | — |

| | Cleansing Phase Example: | | | | |
|---|---|---|---|---|---|
| | 21 | 22 | 23 | 24 | 25 |
| Skin Benefit Components and Thickeners | | | | | |
| Water, distilled | QS | QS | QS | QS | QS |
| Glycerin | 0.3 | 0.3 | 1.93 | — | — |
| Guar hydroxypropyl-trimonium chloride(N-Hance 3196 or Jaguar C-17, Rhodia) | 0.4 | 0.4 | 0.2 | 0.6 | 0.6 |
| Polyquaternium-10 (UCARE JR-30M from Aqualon) | — | — | — | — | — |
| PEG 90M (Polyox WSR 301) | 0.10 | 0.10 | 0.15 | 0.15 | 0.15 |
| PEG 14M (WSR N-3000 H) | — | — | — | — | — |
| Citric acid | — | — | 0.25 | 0.25 | 0.25 |
| Surfactant Components | | | | | |
| Sodium trideceth sulfate (Cedepal TD-403, Stepan Co.) | — | — | 6.17 | 7.9 | 7.9 |
| ALS | 13.42 | 9.40 | 9.26 | 7.9 | 7.9 |
| AES | — | — | — | | |

-continued

| | | | | | |
|---|---|---|---|---|---|
| Sodium LAA | — | — | 4.57 | 4.7 | 4.7 |
| Polyoxyethylene 2.5 lauryl alcohol (Arylpon F, Cognis) | 3.0 | 2.1 | — | — | — |
| Cocobetaine | 3.7 | 2.6 | — | — | — |
| Isosteareth-2 (Hetoxol IS-2, Global Seven Inc, NJ, USA) | — | — | 1.0 | 1.0 | 1.0 |
| Preservative and Minors | | | | | |
| Fragrance/perfume | 1.4 | 1.4 | 1.54 | 1.54 | 1.44 |
| Sodium chloride | 3.5 | 3.5 | 3.5 | 3.5 | 3.5 |
| Disodium EDTA | 0.06 | 0.06 | 0.12 | 0.12 | 0.12 |
| DMDM Hydantoin (Glydant) | 0.73 | 0.73 | 0.37 | 0.37 | 0.37 |
| Sodium benzoate | — | — | 0.2 | 0.2 | 0.2 |
| Titanium dioxide | — | — | — | — | — |
| Lauric Acid | — | — | — | — | — |
| Trihydroxystearin (Thixcin R) | — | — | — | — | — |
| Expancel 091 DE d30 | 0.3 | 0.3 | 0.3 | 0.3 | 0.3 |
| Polymeric Phase Structurants | | | | | |
| Xanthan gum (Keltrol CGT) | 0.13 | 0.26 | 0.4 | 0.2 | 0.2 |
| Acrylates/Vinyl Isodecanoate Crosspolymer (Stabylen 30) | 0.27 | 0.54 | — | — | — |
| Final pH | 5.9 | 5.9 | 6.0 | 6.0 | 6.0 |
| Total surfactant, % of cleansing phase | 20.1 | 14.1 | 21.0 | 21.5 | 21.5 |
| Anionic surfactant, % of surfactant component | 67 | 67 | 74 | 74 | 74 |
| Mono methyl branched anionic surfactant, % of anionic surfactant | 0 | 0 | 0– | 0 | 0 |
| Branched anionic surfactant, % of anionic surfactant | 0 | 0 | 40 | 50 | 50 |
| Zero shear viscosity, Pa-sec | 6800 | 7600 | 8100 | 4900 | 5700 |
| Yield stress, Pa | 14 | | | | |
| Lather Volume of cleansing phase: Flash/Total (ml/ml) | 490/1810 | 500/1930 | 650/2340 | 540/2150 | 510/2020 |
| Structured phase volume, % | 64 | 52 | 91 | 86 | 88 |
| Stability: % Third Phase | 0 | 6 | 0 | 0 | 0 |
| T-bar % viscosity change | −23 | −37 | −18 | −15 | −7 |

| | Cleansing Phase Example: | | | | |
|---|---|---|---|---|---|
| | 26 | 27 | 28 | 29 | Comparative Example 30 |
| Skin Benefit Components and Thickeners | | | | | |
| Water, distilled | QS | QS | QS | QS | QS |
| Glycerin | — | — | 0.21 | 0.21 | 0.3 |
| Guar hydroxypropyl-trimonium chloride (N-Hance 3196 or Jaguar C-17, Rhodia) | 0.45 | 0.45 | 0.47 | 0.47 | 0.4 |
| PEG 90M (Polyox WSR 301) | 0.15 | 0.15 | 0.07 | 0.07 | 0.1 |
| Citric acid | 0.25 | 0.25 | 0.25 | 0.25 | 0.2 |
| Surfactant Components | | | | | |
| Sodium trideceth sulfate (Cedepal TD-403, Stepan Co.) | | 5.6 | 5.56 | 5.65 | |
| *Sulfated Neodol ™ 23, sodium salt | — | — | — | 5.65 | — |
| *Ethoxylated Safol ™ 23 (3 mol EO) sulfate, sodium salt | 3.73 | — | — | — | — |
| *Sulfated Safol ™ 23 sodium salt | 1.87 | | 5.56 | | |
| ALS | 8.4 | 8.4 | — | — | — |
| AES | — | — | — | — | 9.4 |
| Sodium Lauroamphoacetate (Miranol L-32 from Rhodia) | 3.0 | 3.0 | — | — | — |
| Polyoxyethylene 2.5 lauryl alcohol (Arylpon F, Cognis) | 1.25 | 0.75 | 2.35 | 2.35 | 2.1 |
| Cocobetaine | — | — | 3.35 | 3.35 | 2.58 |
| Isosteareth-2 (Hetoxol IS-2, Global Seven Inc, NJ, USA) | 1.0 | 1.0 | 1.0 | 1.0 | — |
| Preservative and Minors | | | | | |
| Fragrance/perfume | 1.44 | 1.44 | 1.54 | 1.54 | 1.4 |
| Sodium chloride | 3.5 | 3.5 | 3.5 | 3.5 | 3.5 |
| Disodium EDTA | 0.12 | 0.12 | 0.12 | 0.12 | 0.06 |
| DMDM Hydantoin (Glydant) | 0.37 | 0.37 | 0.37 | 0.37 | 0.7 |
| Sodium benzoate | 0.2 | 0.2 | 0.2 | 0.2 | |

-continued

| | | | | | |
|---|---|---|---|---|---|
| Expancel 091 DE d30 microspheres (Akzo Nobel) | 0.3 | 0.3 | 0.3 | 0.3 | 0.3 |
| Polymeric Phase Structurants | | | | | |
| Xanthan gum (Keltrol CGT) | 0.4 | 0.4 | 0.66 | 0.66 | 0.26 |
| Acrylates/Vinyl Isodecanoate Crosspolymer (Stabylen 30) | — | — | — | — | 0.54 |
| Final pH (adjust to) | 6.0 | 6.0 | 6.2 | 6.0 | 5.9 |
| Total surfactant, % of cleansing phase | 19.25 | 18.75 | 17.82 | 18.0 | 14.08 |
| Anionic surfactant, % of surfactant component | 73 | 75 | 62 | 63 | 67 |
| Monomethyl branched anionic surfactant, % of anionic | 40% | 0% | 50% | 50% | 0% |
| Branched anionic surfactant, % of anionic surfactant | 40% | 40% | 100% | 100% | 0% |
| Zero shear viscosity, Pa-sec | 3400 | 4600 | 4500 | 4100 | 900 |
| Lather Volume of cleansing phase: Flash/Total (ml/ml) | | 590/2250 | 520/1910 | 520/2020 | 470/1920 |
| Structured Domain Volume Ratio, % | 88 | 87 | — | — | — |
| Stability: % Third Phase | 0 | 0 | 0 | 0 | 5% |
| T-bar % viscosity change | −22 | −20 | −29 | −38 | −79 |

*Sulfation to >95% completion of Neodol ™ 23, Safol ™ 23, and Safol ™ 23-3 was performed in a falling film tube reactor using a continuous SO$_3$/air process, neutralizing the product with sodium hydroxide, leaving 2.5% or less unreacted alcohol, by The Procter & Gamble Co, Ivorydale Technical Center, Cincinnati, Ohio, USA. Cocamidopropyl betaine (Cocobetaine) is always Tegobetaine F from DeGussa, Inc. Ammonium Lauryl Sulfate (ALS) and Ammonium Laureth Sulfate (AES) are from The Procter & Gamble Co., and AES is 3 mole ethoxylated. SLS and SLES are the sodium salts. Sodium LAA is sodium lauroamphoacetate, Miranol L-32 Ultra (Rhodia).

The cleansing phase can be prepared by conventional mixing techniques. First the water is added and skin benefit components and thickeners to a mixing vessel and agitated until a homogeneous dispersion is formed. Then add in the following sequence: surfactants, Disodium EDTA, preservative and half the sodium chloride and all other preservatives and minors except fragrance and the withheld sodium chloride. Heat to 65-70° C. if Cocamide monoethanolamine (CMEA) is used, otherwise maintain at ambient temperature while agitating. Cool to 45° C. if heating was used. For additional stability, gas filled microspheres having a density of about 30 kg/m$^3$ such as Expancel 091 DE 40 d30 (from Expancel, Inc., Duluth, Ga.) can optionally be used at about 0.1-0.5% of the batch. In a separate vessel, prewet the structuring polymers with fragrance and add to the mix vessel at the same time as the remaining sodium chloride while agitating. Agitate until homogeneous. Adjust pH using citric acid and/or NaOH to 5.8-6.2 unless specified otherwise, then pump through a static mixing element to disperse any lumps to complete the batch. Coacervate amount is measured by thoroughly mixing (shake) 23 ml distilled water with 2 ml surfactant in a 25 ml graduated cylinder (e.g., Pyrex No. 3255) and allowing it to stand undisturbed for 1 week at 75° F., observing the amount of turbid phase at the bottom, measuring in ml or if less than 1 ml, measuring in height from the bottom.

Examples 31-39

For the following examples 31-39, the cleansing phase which is Example 1 is prepared except fragrance is withheld from the composition. The composition is denoted Fragrance Free Cleansing Phase 1 in the following examples and is shown as total weight added, not chemical weight. Examples 21-26 are prepared by prewetting the polymer component with the fragrance, blending the polymer-fragrance mixture with an equal weight of the fragrance free cleansing phase by hand using a spatula to prepare a paste, adding the remaining cleansing phase and stirring, adding additional water last and stirring by hand in small quantities (e.g., 75 gm total being prepared in about a 5 minute period). After preparation, the Examples are examined and found to be free of detectable lumps by eye and to the touch. Examples 27-29 are prepared by dispersing the polymer in water with high shear until free of lumps, then blending the mixture by vigorous hand stirring with the fragrance free cleansing phase and fragrance until homogeneous, about 2 minutes. The example compositions are then lightly centrifuged (3 min, 2,500 rpm in the mix jars) to deareate.

| | Example: | | | | |
|---|---|---|---|---|---|
| zip | 31 (control) | 32 | 33 | 34 | 35 |
| Fragrance Free Cleansing Phase 1 | 73.75 | 70.8 | 70.8 | 70.8 | 70.8 |
| Fragrance | 0.625 | 0.60 | 0.60 | 0.60 | 0.60 |
| Hydroxy-propyl starch phosphate (Structure XL, National Starch Co.) | — | 4.0 | — | — | — |

-continued

|  |  |  |  |  |  |
|---|---|---|---|---|---|
| Guar gum (Supercol U, Hercules Inc. Aqualon Div.) | — | — | 4.0 | — | — |
| Hydroxyethyl-cellulose (250MR, Aqualon) | — | — | — | 4.0 | — |
| Carboxymethyl-cellulose (9M31XF, Aqualon) | — | — | — | — | 4.0 |
| Distilled Water | 25.625 | 24.6 | 24.7 | 24.7 | 24.7 |
| % Surfactant component | 17.73 | 17.02 | 17.02 | 17.02 | 17.02 |
| Zero Shear Viscosity (Pa-sec) | 4,480 | 11,020 | 9,950 | 12,300 | 11,800 |
| Yield Stress (Pa) | 1.8 | 6.0 | 20.3 | 21.0 | 20.0 |

|  | Example: | | | |
|---|---|---|---|---|
|  | 36 | 37 | 38 | 39 |
| Fragrance Free Cleansing Phase 1 | 70.8 | 65.47 | 65.57 | 65.57 |
| Fragrance | 0.60 | 1.64 | 1.64 | 1.64 |
| Starch octenylsuccinate (NCreamer46, National Starch) | 4.0 | — | — | — |
| PEG-150/Decyl Alcohol/SMDI Copolymer (Aculyn 44, Rohm & Haas) | — | 0.98 | — | — |
| Cetyl hydroxyethyl-cellulose (CS330, Aqualon) | — | — | 0.66 | — |
| PEG-180/Laureth-50/TMMG Copolymer (Pure Thix 1450, Sud-Chemie) | — | — | — | 0.16 |
| Distilled Water | 24.7 | 31.91 | 32.13 | 32.63 |
| % Surfactant component (calculated) | 17.02 | 15.74 | 15.76 | 15.76 |
| Zero Shear Viscosity (Pa-sec) | 5,380 | 13,580 | 6,810 | 6,800 |
| Yield Stress (Pa) | 1.8 | 17.0 | 13.0 | 23.0 |

Structured Aqueous Phase

The Structured Aqueous Phase of Examples 40-41 can be prepared by dispersing polymers in water with high shear, adding salt and remaining ingredients except petrolatum and mineral oil, neutralizing to pH 7.0 with triethanolamine (approximate TEA level is shown), heating to 50° C., adding the petrolatum and mineral oil as a liquid at 80° C., and agitating until homogeneous without high shear. Pigments having no water soluble components are preferably used. A particle size of about 5-100 microns for the petrolatum component is obtained for most of the particles.

|  | Structured Aqueous Phase (Non-Lathering) Example: | |
|---|---|---|
|  | 40 | 41 |
| Water, distilled | QS | QS |
| Acrylates/Vinyl Isodecanoate Crosspolymer (Stabylen 30 from 3V) | 1.0 | 0.8 |
| Xanthan gum (Keltrol CGT or Keltrol 1000 from Kelco) | 1.0 | 0.8 |
| DMDM Hydantoin, preservative | 0.4 | 0.4 |
| EDTA | 0.05 | 0.04 |
| Mineral oil (Hydrobrite 1000, Witco) | 0.03 | 4.82 |
| Petrolatum (Super White Protopet, Witco) | 20.0 | 18.78 |
| Triethanolamine | 0.80 | 0.80 |
| Sodium chloride | 3.0 | 2.4 |
| Pigment | 0.35 | 0.35 |

Benefit Phase

Benefit phases can be prepared having the following ingredients. The benefit phase can be prepared by adding petrolatum into a mixing vessel. Heat to 190° F. (88° C.). Add mineral oil and particles. Shear the batch to ensure good pigment dispersion. Agitate the batch and slowly cool down to ambient temperature. Pigments having no water soluble components are preferably used. A particle size of about 5-100 microns for the petrolatum component is obtained for most of the particles.

|  | Benefit Phase Example: | | |
|---|---|---|---|
|  | 42 | 42 | 44 |
| Mineral oil (Hydrobrite 1000, Witco) | — | 30.0 | 30.0 |
| Petrolatum (Super White Protopet, Witco) | — | — | 69.95 |
| Petrolatum (G2218, Witco) | 99.95 | 69.95 | — |
| Pigment | 0.05 | 0.05 | 0.05 |

Petrolatum can be obtained from Witco division of Crompton Corporation (Petrolia, Pa., USA). G2218 petrolatum has a complete melting point of about 139 degrees Fahrenheit, a Saybold viscosity of between about 75-86 SUS at 210° F., a Penetration of between 192-205 dmm, a Consistency Value of about 42 Pa-s with a shear index of about 0.53, a Structure Rigidity of 370 Pa and a Flow Onset Temperature of 109.8° F. A gas chromatogram of the petrolatum indicates hydrocarbons between C20 and C120 are present. Taking the ratio of the average peak heights of the GC for hydrocarbons having even numbered chain lengths from C22-28, C44-50 and C94-116, the petrolatum has a ratio of peak heights of about 0.72:1.0:0.32. Hydrobrite 1000 has a high viscosity relative to nearly all mineral oils.

Compositions

The multi-phase personal care compositions can be prepared by the following procedure. When the benefit phase is lipid continuous, e.g., from Examples 33, 34, and 35, the benefit phase is maintained at 80° C. in a separate tank which is recirculated through a scraped wall heat exchanger having an outlet temperature of 45° C. Lipid at 45° C. is pumped either to the filling operation or back to the recirculation tank. When the Structured Aqueous Phase is used in place of the benefit phase, the phase is water continuous, and is maintained in a hopper and gravity fed to the filling operation. Cleansing phase is maintained at ambient temperature in a gravity fed tank above the filler. Cleansing Phase and Benefit Phase or Structured Aqueous Phase are simultaneously pumped in a specified volumetric ratio, including 80:20, 70:30, 50:50 and 40:60 Cleansing Phase:Benefit Phase and/or Cleansing Phase:Structured Aqueous Phase through ¾ in. diameter pipes containing a 1,2,3 or 4-element static mixer (Koch/SMX type), the single pipe exits into a 10 oz. bottle on a spinning platform. The platform is set to 325 rpm spin speed, the composition filling 315 ml in about 2.0 seconds, the spinning platform being lowered during filling so that filling proceeds in a layering fashion from bottom to top. An even, relatively horizontal striped pattern is obtained. By adjusting temperature and viscosity of the phases, static mixer element types and number of elements, pipe diameters, spin rates, etc., a wide variety of patterns can be obtained.

Additionally, the present invention can be prepared by the method and apparatus as disclosed in U.S. Pat. No. 6,213,166 issued to Thibiant, et al on Apr. 10, 2001, which method and apparatus allows compositions to be filled with a spiral configuration into a single container using at least 2 nozzles.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-phase personal care composition comprising:
   a. a first visually distinct structured cleansing phase comprising:
      i. from about 2% to about 21% by weight of said first visually distinct structured cleansing phase, comprising at least one branched anionic surfactant;
      ii. from about 0.5% to about 5.0%, by weight of said first visually distinct structured cleansing phase, of a nonionic surfactant having an HLB from about 3.4 to about 15.0 selected from the group consisting of ethoxylated alcohols, glyceryl monohydroxystearate, steareth-2, laureth-2, isosteareth-2, propylene glycol stearate, PEG-2 stearate, sorbitan monostearate, glyceryl stearate, glyceryl laurate and mixtures thereof;
      iii. 3.0% or greater, by weight of said first visually distinct structured cleansing phase, of an amphoteric or zwitterionic surfactant;
      iv. from about 1% to about 6% by weight of said first visually distinct structured cleansing phase of an electrolyte;
      vi. from about 0.1% to about 0.5% by weight of said first visually distinct structured cleansing phase, of gas filled microspheres; and
   b. a second visually distinct benefit phase.

2. The multi-phase personal care composition of claim 1, wherein said branched anionic surfactant is selected from the group consisting of sodium trideceth sulfate, sodium tridecyl sulfate, ammonium trideceth sulfate, ammonium tridecyl sulfate, monomethyl branched surfactants and mixtures thereof.

3. The multi-phase personal care composition of claim 1, wherein said branched anionic surfactant comprises monomethyl branched surfactants.

4. The multi-phase personal care composition of claim 1, wherein said cleansing phase provides a Yield Stress of greater than about 1.5 Pascal.

5. The multi-phase personal care composition of claim 1, wherein said composition further comprises a polymeric phase structurant.

6. The multi-phase personal care composition of claim 5, wherein said polymeric phase structurant is selected from the group consisting of deflocculating polymers, naturally derived polymers, synthetic polymers, crosslinked polymers, block polymers, block copolymers, copolymers, hydrophilic polymers, nonionic polymers, anionic polymers, hydrophobic polymers, hydrophobically modified polymers, associative polymers, oligomers, and mixtures thereof.

7. The multi-phase personal care composition of claim 5, wherein said composition comprises from about 0.05% to about 10%, by weight of said cleansing phase, of said polymeric phase structurant.

8. The multi-phase personal care composition of claim 1, wherein said second visually distinct phase is a benefit phase comprises hydrophobic material with a Vaughan Solubility Parameter of from about 5 to about 15.

9. The structured multi-phase personal care composition of claim 1, wherein said benefit phase has a Consistency Value (K) of from about 30 to about 350 Pa-s.

10. The structured multi-phase personal care composition of claim 1, wherein said first visually distinct phase and said second visually distinct phase form a pattern.

11. The structured multi-phase personal care composition of claim 10, wherein said pattern is selected from the group consisting of striped, geometric, marbled, and combinations thereof.

12. The structured multi-phase personal care composition of claim 10, wherein said composition is packaged in a container such that said pattern is visible through said container.

13. The structured multi-phase personal care composition of claim 1, wherein said cleansing phase further comprises a liquid crystalline phase inducing structurant.

14. The structured multi-phase personal care composition of claim 13, wherein said liquid crystalline phase inducing structurant is selected from the group consisting of fatty acids, fatty alcohols, fatty esters, trihydroxystrearin, and mixtures thereof.

15. The structured multi-phase personal cleansing composition of claim 1, wherein said composition further comprises a optional benefit component, wherein said benefit component are selected from the group consisting of emollients, particles, beads, skin whitening agents, fragrances, colorants, vitamins and derivatives thereof, sunscreens, preservatives, anti-acne medicaments, antioxidant, chelators, essential oils, skin sensates, antimicrobial, and mixtures thereof.

* * * * *